United States Patent
Coughlan

(10) Patent No.: US 6,566,584 B1
(45) Date of Patent: May 20, 2003

(54) COMPOSITIONS AND METHODS FOR ALTERING AN ACETYL-COA METABOLIC PATHWAY OF A PLANT

(75) Inventor: Sean J. Coughlan, Hockessin, DE (US)

(73) Assignee: Pioneer Hi-Bred International, Inc., Des Moines, IA (US)

(*) Notice: Subject to any disclaimer, the term of this patent is extended or adjusted under 35 U.S.C. 154(b) by 0 days.

(21) Appl. No.: 09/377,307

(22) Filed: Aug. 19, 1999

Related U.S. Application Data

(60) Provisional application No. 60/097,255, filed on Aug. 20, 1998.

(51) Int. Cl.[7] .................. C12N 15/82; C12N 5/10; C12N 15/29; A01H 5/00; A01H 5/10
(52) U.S. Cl. ............... 800/281; 800/278; 536/23.6; 435/419; 435/468; 435/332
(58) Field of Search ................. 436/6, 468, 410, 436/419, 320.1, 332; 536/23.1, 24.1, 24.5; 800/278, 292, 293, 294, 295, 298, 320.1

(56) References Cited

U.S. PATENT DOCUMENTS

| | | | |
|---|---|---|---|
| 5,194,596 A | * | 3/1993 | Tischer .................. 530/399 |
| 5,350,836 A | * | 9/1994 | Kopchick et al. ........... 530/399 |
| 5,498,544 A | | 3/1996 | Gengenbach et al. |
| 5,559,220 A | | 9/1996 | Roessler et al. |
| 5,679,881 A | | 10/1997 | Metz et al. |
| 2002/0162137 A1 | | 10/2002 | Nikolau et al. |

FOREIGN PATENT DOCUMENTS

| | | |
|---|---|---|
| DE | 4317260 A1 | 7/1994 |
| WO | WO96/31609 | 10/1996 |
| WO | WO97/07222 | 2/1997 |
| WO | WO97/32986 | 9/1997 |
| WO | WO98/00557 | 1/1998 |
| WO | WO98/05758 | 2/1998 |
| WO | WO98/06831 | 2/1998 |
| WO | WO98/06862 | 2/1998 |

OTHER PUBLICATIONS

Vincenzo De Luca, Molecular characterization of secondary metabolic pathways, Agbiotech News and Information 1993 vol. 5, No. 6, pp. 225N–229N.*

Gregory Stephanopoulos et al., Metabolic engineering—methodologies and future prospects, TIBTECH Sep. 1993 (vol. 11), pp. 392–396.*

Genetwork, TIG Oct. 1996 vol. 12, No. 10, pp. 425–427.*

Errors in genome annotation, TIG Apr. 1999, vol. 15, No. 4, pp. 132–133.*

Temple F. Smith et al., The challenges of genome sequence annotation or "The devil is in the details", Nature Biotechnology, vol. 15, Nov. 1997, pp. 1222–1223.*

C.C.Pilbeam et al., Comparison of the Effects of Various Lenghts of Synthetic Human Parathyroid Hormone–Related Peptide (hPTHrP) of Malignancy on Bone Resorption and Formation in Organ Culture, Bone, 14, pp. 717–720.*

Slobodan Vukicevic et al., Induction of nephrogenic mesenchyme by osteogenic protein 1 (bone morphogenetic protein 7), Proc. Natl. Acad. Sci. USA, vol. 93, pp. 9021–9026.*

(List continued on next page.)

Primary Examiner—Tekchand Saidha
Assistant Examiner—M Schmidt
(74) Attorney, Agent, or Firm—Pioneer Hi-Bred International, Inc.

(57) ABSTRACT

Compositions and methods for altering the content of plant seeds are provided. The compositions comprise nucleotide sequences encoding the enzyme acetyl-CoA synthetase. Such compositions find use in increasing the biosynthesis of fatty acids and/or carotenoids in plants. By expressing the sequences utilizing seed-specific promoters, plant seed can be obtained having increased levels of oils, specialty oils, carotenoids, and amino acids.

8 Claims, 1 Drawing Sheet

OTHER PUBLICATIONS

Laura E. Benjamin et al., A plasticity window for blood vessel remodeling is defined by pericyte coverage of the preformed endothelial network and is regulated by PDGF–B and VEGF, Development 125, pp. 1591–1598.*

Genetwork, Protein annotation: detective work for function prediction, TIG Jun. 1998 vol. 14, No. 6, pp. 248–250.*

Jeffrey Skolnick et al., From genes to protein structure and function: novel applications of computational approaches in the genomic era, Trends in Biotech, 18 (1): pp. 34–39.*

Peer Bork, Powers and Pitfalls in Sequence Analysis: The 70% Hurdle, Genome Research, pp. 398–400.*

James A. Wells, Additivity of Mutational Effects in Proteins, Biochemistry, vol. 29, No. 37, Sep. 18, 1990, pp. 8509–8517.*

J. Thomas Ngo et al., Computational Complexity, Protein Structure Prediction, and the Levinthal Paradox, pp. 491–495.*

Zeiher et al. (1991) "Spinach Leaf Acetyl–Coenzyme ASynthetase: Purification and Characterization", *Plant Physiol.* 96:382–389.

Roughan et al. (1994) "On The Assay Of Acetyl–CoA Synthetase Activity In Chloroplasts And Leaf Extracts", *Analytical Biochemistry* 216:77–82.

Sasaki (1993) "Rice cDNA, Partial Sequence (R1444_1A)", EMBL Accession No.: D24159, XP002126951.

Behal et al. (Jan. 5, 1998) "Arabidopsis Thaliana Acetyl–CoA Synthetase mRNA Complete CDs", EMBL Accession No.:AF036618, XP002126950.

Walbot (Jul. 28, 1999) "614018F08.x1 614—RootcDNA Library From Walbot Lab Zea Mays cDNA, mRNA Sequence", EMBL Accession No.: AI891317, XP002126952.

PCT International Application, dated Jan. 24, 2000, PCT/US99/18011, filed Aug. 13, 1999.

Roughan et al. (1979), "On the Control of Long–Chain–Fatty Acid Synthesis in Isolated Intact Spinach (*Spinacia oleracea*) Chloroplasts", *Biochem J.* 184: 193–202.

Post–Beittenmiller et al., (1992) "Regulation of Lipid Synthesis in Castor Seeds: Analysis of the In Vivo Acyl–Acyl Carrier Protein Pools", *Seed Oils For The Future*, Chapter 6, pp. 45–51.

Kang et al. (1994) Starch and Fatty Acid Synthesis in Plastids From Developing Embryos of Oilseed Rape (*Brassica napus L.*), *The Plant Journal* 6(6):795–805.

Verwoert et al. (1995) "Modification of *Brassica napus* Seed Oil By Expression of the *Escherichia coli fabH* Gene, Encoding 3–ketoacyl–acyl Carrier Protein Synthase III", *Plant Molecular Biology* 27:875–886.

Kang et al. (1994) "TheActivity of Acetyl–CoA Carboxylase Is Not Correlated With The Rate Of Lipid Synthesis During Development of Oilseed Rape (*Brassica napus L.*) Embryos", *Plants* 193:320–325.

Smith et al. (1992) "Malate– and Pyruvate–Dependent Fatty Acid Synthesis In Leucoplasts From Developing Castor Endosperm", *Plant Physiol.* 98:1233–1238.

Nagiec et al. (1993) "A Suppressor Gene That Enables *Saccharomyces cerevisiae* to Grow Without Making Sphingolipids Encodes A Protein That Resembles An *Escherichia coli* Fatty Acyltransferase", *The Journal of Biological Chemistry* 268(29):22156–22163.

Roughan et al. (1994), "On the Assay of Acetyl–CoA Synthetase Activity In Chloroplasts and Leaf Extracts", *Analytical Biochemistry* 216:77–82.

Golz et al. (1993), "Isolation and Characterization of Acetyl–CoA Synthetase From Etiolated Radish Seedlings", *J. Plant Physiol.* 141:276–280.

Amino Acid Sequence Alignment, *Zea mays*, and *D. melangaster* Acetyl–CoA synthetases.

* cited by examiner

COMPOSITIONS AND METHODS FOR ALTERING AN ACETYL-COA METABOLIC PATHWAY OF A PLANT

CROSS-REFERENCE TO RELATED APPLICATIONS

This application claims the benefit of U.S. Provisional Application No. 60/097,255, filed Aug. 20, 1998.

FIELD OF THE INVENTION

The invention relates to the genetic manipulation of plants, particularly to altering metabolic end products in plants and plant seeds.

BACKGROUND OF THE INVENTION

A long time goal of scientists has been to improve the fatty acid profile for oils. The oxidative stability of the vegetable oil is related to the number of double bonds in its fatty acids. That is, molecules with several double bonds are recognized to be more unstable. Thus, scientists have attempted to reduce the amount of alpha-linolenic acid in order to improve shelf life and oxidative stability. Unfortunately, the use of naturally occurring germplasm has not proven to be successful by traditional breeding mechanisms.

Other work has concentrated on producing modified oils with specific fatty acid composition, particularly very high oleic acid oils. High-oleic canola, safflower, and sunflower oils as well as low-linolenic canola and soybean oils are on the market, although in limited quantities.

Modified oils are needed because of the stability as well as for health concerns. For example, high-oleic sunflower oil has about ⅓ the saturated fat content of cottonseed oil.

A major source of fatty acids is biosynthesis from small-molecule intermediates derived from metabolic breakdown of sugars, some amino acids, and other fatty acids. Acetyl-CoA is the direct source of all carbon atoms for the synthesis of palmitic acid. In a majority of instances the saturated straight-chain C16 acid, palmitic acid, is first synthesized and all other fatty acids are made by modification of palmitic acid. Fatty acids are synthesized by sequential addition of 2-carbon units to the activated carboxyl end of a growing chain.

Acetyl-CoA Carboxylase (ACCase) catalyzes the formation of malonyl-CoA from acetyl-CoA and bicarbonate in animal, plant, and bacterial cells. Malonyl-CoA is an essential substrate for (i) de novo fatty acid synthesis, (ii) fatty acid elongation, (iii) synthesis of secondary metabolites such as flavonoids and anthocyanins, and (iv) malonylation of some amino acids and secondary metabolites. Synthesis of malonyl-CoA is the first committed step of flavonoid and fatty acid synthesis and current evidence suggests that ACCase catalyzes the primary regulatory or rate-limiting step of fatty acid synthesis. Formation of malonyl-CoA by ACCase occurs via two partial reactions and requires a biotin prosthetic group:

E-biotin+ATP+$HCO_3$→E-biotin-$CO_2$+ADP+Pi (ii) E-biotin-$CO_2$+Acetyl-CoA→E-biotin+malonyl-CoA

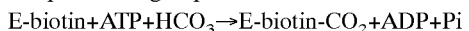

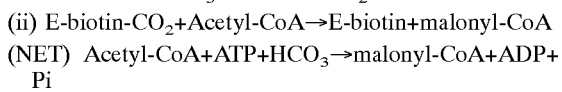

In bacteria such as *Escherichia coli*, the ACCase has four distinct, separable protein subunit components; a biotin carboxyl carrier protein, a biotin carboxylase and two subunits of carboxyltransferase. In eukaryotes, ACCase is composed of multimers of a single multifunctional polypeptide having a molecular mass typically greater than 200 kDA (Samols et al., *J. Biol. Chem.* 263:6461–6464 (1988)). These multimers have molecular masses ranging from 400 kDa to 8 MDa.

De novo fatty acid synthesis in chloroplasts involves successive 2-carbon additions to acetate, using malonate as the 2-C donor. All intermediates are attached to acyl carrier protein (ACP). Synthesis in plastids resembles that in *E. coli* in that the fatty acid synthesis complex can be dissociated into separate enzymes: β-ketoacyl-ACP synthase (KAS), β-ketoacyl-ACP reductase, β-hydroxyl-ACP dehydratase, and enoyl-ACP reductase, acetyl-CoA:ACP transacylase, and malonyl-CoA:ACP transacylase. A highly active KASIII isozyme catalyzes the condensation of acetyl-CoA and malonyl-ACP. Successive additions of malonyl-CoA to acyl-ACPs catalyzed by KASI form C16 acyl-ACP, some of which is converted to C18 acyl-ACP by KASII and then to C18:1-ACP. Fatty acid metabolism then diverges. De-esterification allows movement to the cytoplasm (eukaryotic path) where fatty acids may be further unsaturated and/or elongated by additions of malonyl-CoA in the ER. Alternatively, fatty acids are linked to glycerol-3 phosphate (prokaryotic path), further unsaturated, and used for synthesis of chloroplast lipids. A portion of cytoplasmic lipids returns to the chloroplast. The relative contributions of these two paths are species-specific but appear to be relatively flexible in mutants blocked in either path. In oil-storing organs such as cotyledons and monocot embryos, the triacylglycerides are stored in cytoplasmic oil bodies surrounded by a single unit membrane.

Lipids, particularly triglycerides, have a great deal of commercial value in food and industrial products. Sunflower, safflower, rape, olive, soybean, peanut, flax, castor, oil palm, coconut and cotton are examples of major crops which are grown primarily or secondarily for their lipids. All agricultural animals provide animal sources for commercial fats and oils.

Seeds contain oil, starch, and protein in proportions which depend upon the plant species, cultivar and the stage of development. In the mature seed of oil seed rape, the main storage products are oil and protein, but starch accumulates transiently during the early phase of oil deposition. In non-photosynthetic tissues the synthesis of starch and fatty acids occurs in the plastids and requires the supply of carbon precursors from the cytosol.

There is needed a method for producing significant levels of fatty acids, carotenoids and other metabolic products in plants, particularly plant seeds. Such altered seeds would be useful nutritionally as well as provide a source for specialty oils and compounds.

SUMMARY OF THE INVENTION

Compositions and methods for modulating a metabolic pathway of a cell, particularly those pathways utilizing acetyl-CoA as a starting material, are provided. Such metabolic pathways include fatty acid biosynthesis, synthesis of isoprenoid compounds, and production of amino acids. The compositions comprise nucleotide sequences encoding the enzyme acetyl-CoA synthetase (ACS). ACS catalyzes formation of acetyl-CoA. Acetyl-CoA is a precursor to fatty acids in plastids through a four-step process using the substrate acetate.

The compositions and methods find use in increasing biosynthesis of fatty acids and/or carotenoids in plants. Thus, utilizing the methods of the invention, seed can be obtained having increased levels of oils, specialty oils, carotenoids, and amino acids genetically altering the content of seed. The methods involve preparing expression constructs with the nucleotide sequences of the invention and the utilization of such constructs to prepare plants having altered metabolic pathways.

The nucleotide sequences of the invention can be used in combination with other genes and antisense sequences to alter the content of a plant seed. In this manner plant seeds having high oil content, specialty oils, increased essential amino acids, carotenoids and other metabolites can be obtained.

DETAILED DESCRIPTION OF THE INVENTION

Figure 1:
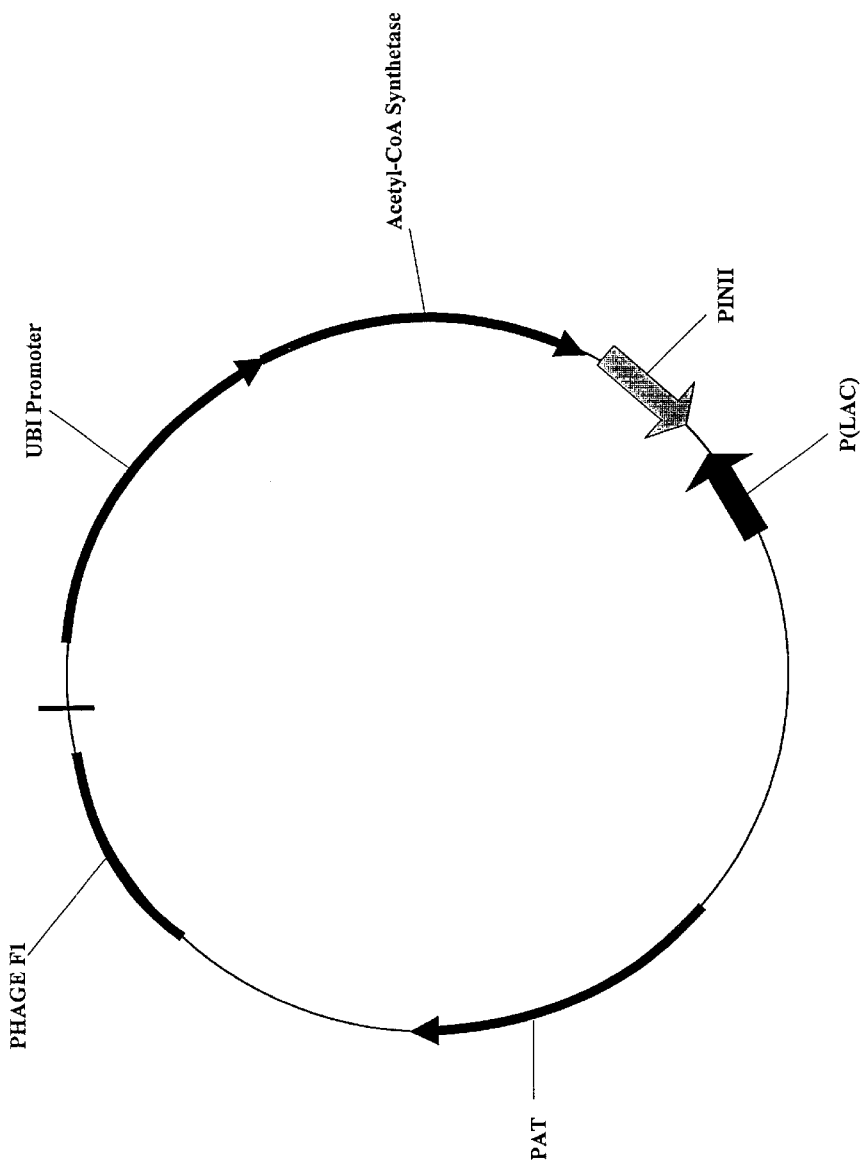
FIG. 1 provides a plasmid for the expression of acetyl-CoA synthetase using a ubiquitin promoter.

In accordance with the subject invention, methods for modulating a metabolic pathway of a cell, particularly pathways utilizing acetyl-CoA as a substrate, hereinafter "acetyl-CoA pathways" are provided. Acetyl-CoA pathways are those pathways utilizing acetyl-CoA as a starting material and include fatty acid biosynthesis, isoprenoid biosynthesis, and production of amino acids. Thus, the methods of the invention provide for increasing and altering fatty acids, carotenoids, and/or amino acids in a plant, particularly plant seeds. The method involves transforming a plant with at least one gene encoding the enzyme acetyl-CoA synthetase (ACS). The plant may also comprise at least one additional gene, a second gene, that can be utilized to shunt the acetyl-CoA into the metabolic pathway of choice or to block a metabolic pathway for the production of other metabolites.

Compositions of the invention include two maize acetyl-CoA synthetase enzymes that are involved in catalyzing the formation of acetyl-CoA. In particular, the present invention provides for isolated nucleic acid molecules comprising nucleotide sequences encoding the amino acid sequences shown in SEQ ID NOS: 2 and 4. Further provided are polypeptides having an amino acid sequence encoded by a nucleic acid molecule described herein, for example those set forth in SEQ ID NOS: 1 and 3 and fragments and variants thereof.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Acetyl-CoA synthetase is a key enzyme in plastids of higher plants which provides the starting substrate in acetyl-CoA for de novo fatty acid biosynthesis. ACS exhibits a high substrate specificity for acetate as compared to other organic acids. ACS plays a central role in several biosynthetic pathways. Besides de novo fatty acid biosynthesis, ACS is needed for the synthesis of mevalonic acid and isoprenoid lipids as well as branched-chain amino acids. Thus, it is recognized that the methods of the invention find use in altering a metabolite of interest in a plant, particularly in a plant seed. For purposes of the invention metabolites include fatty acids, carotenoids, and amino acids.

By increasing the biosynthesis of a metabolite is intended that the levels are increased over the levels in a native untransformed seed. That is, the levels are increased at least 2 fold to at least 10 fold in the transformed seed. In some instances significant increases of the metabolite can be obtained.

By "significant increase" is intended at least about a 10 to about a 50 fold increase, preferably at least about a 25 to about a 50 fold increase, more preferably about a 25 to about a 100 fold increase. Thus, the seed of the invention is a significant source of the metabolite, fatty acid, carotenoid, or amino acids of interest.

The synthesis of acetyl-CoA, catalyzed by ACS is the first step in the synthesis of long-chain fatty acids from exogenous acetate by isolated, illuminated chloroplasts. Chloroplasts have been shown to be the sole repository of ACS in spinach cells. ACS activity has been detected in all chloroplast preparations so far examined and where comparison can be made, its activity normally exceeds that of pyruvate dehydrogenase by at least two-to five-fold. Additionally, in almost every case where comparisons have been made, acetate has been shown to be the preferred substrate for chloroplast fatty acid synthesis. The presence of acetate in incubations has strongly inhibited the incorporation of other precursors into fatty acids.

As acetyl-CoA in plant cells provides the starting substrate for key metabolic pathways, transformation of the plant cell with a nucleotide sequence encoding an acetyl-CoA synthetase results in increased metabolic activity. By transforming the plant with at least a second gene, the acetyl-CoA can be shunted into the particular metabolic pathway of choice. For example, for the production of fatty acids, the second gene may comprise nucleic acid sequence encoding acetyl-CoA carboxylase (ACCase). See, for example, WO 98/05758. Transformation with a second gene encoding an enzyme in the fatty acid pathway leads to a significant increase in the flux for the production of fatty acids. That is, there is an increase in the metabolic activity that can be further manipulated for the production of increased and/or altered fatty acid composition in the transformed seed.

To further increase the flux into fatty acid biosynthesis, an antisense construct for a nucleotide sequence encoding a protein in the carotenoid pathway can be utilized. Such nucleotide sequences include, IPP isomerase (Hahn et al. (1996) *J. Bacteriol.* 178:619–624 and the references cited therein, GenBank Accession Nos. U48963 and X82627, GenBank Accession No. U48962, GenBank Accession No. U4896 1, GenBank Accession No. X 14230); geranylgeranyl pyrophosphate synthase (Misawa et al. (1990) *J. Bacteriol.* 172:6704–6712 and Application WO 91/13078); phytoene synthase (Misawa et al. (1990) *J. Bacteriol.* 172:6704–6712, GenBank Accession No. D90087, Application WO 91/13078, Armstrong et al. (1989) *Mol. Gen. Genet.* 216:254–268, Armstrong, G. A. "Genetic Analysis and Regulation of Carotenoid Biosynthesis." In R. C. Blankenship, M. T. Madigan, and C. E. Bauer (ed.), *Anoxygenic photosynthetic bacteria; advances in photosynthesis.* Kluwer Academic Publishers, Dordrecht, The Netherlands, Armstrong et al. (1990) *Proc. Natl. Acad. Sci. USA* 87:9975–9979, Armstrong et al. (1993) *Methods Enzymol.* 214:297–311, Bartley and Scolnik (1993) *J. Biol. Chem.* 268:27518–27521, Bartley et al. (1992) *J. Biol. chem.* 267:5036–5039, Bramley et al. (1992) *Plant J.* 2:291–343, Ray et al.(1992) *Plant Mol. Biol.* 19:401–404, Ray et al. (1987) *Nucleic Acids Res.* 15:10587, Romer et al. (1994) *Biochem. Biophys. Res. Commun.* 196:1414–1421, Karvouni et al. (1995) *Plant Molecular Biology* 27:1153–1162, GenBank Accession Nos. U32636, Z37543, L37405, X95596, D58420, U32636, Z37543, X78814, X82458, S71770, L27652, L23424, X68017, L25812, M87280, M38424, X69172, X63873, and X60441, Armstrong, G. A. (1994) *J. Bacteriol.* 176:4795–4802 and the references cited therein); and, phytoene desaturase (Misawa et al. (1990) *J. Bacteriol.* 1 72:6704–6712, Application WO 91/13078, GenBank Accession Nos. L37405, X95596, D58420, X82458, S71770, and M87280). See, also, Misawa et al. (1990) *J. of Bacteriology* 172:6704–6712, E. P. 0393690 B1, U.S. Pat. No. 5,429,939, Bartley et al. (1992) *J. Biol. Chem.* 267:5036–5039, Bird et al. (1991) *Biotechnology* 9:635–639, and U.S. Pat. No. 5,304,478, which disclosures are herein incorporated by reference.

Once the pathway for fatty acid biosynthesis has been primed, additional coding sequences in the fatty acid biosynthesis pathway and corresponding antisense sequences can be used for the production of a high concentration of specialty oils. See, for example, Poulose et al. (1985) *J. Biol. Chem.* 260:15953–15958 (S-acyl fatty acid synthase); Bayley et al. (1988) *BioTechnology* 6:1219–1221 (medium chain hydrolase gene); Mizamoto et al. (1988) *J. Biol. Chem.* 265:13393–13399 (fatty acid reductase); Naggert et al. (1987) *Biochem. J.* 243:597–601 (S-acyl fatty acid synthase thioester hydrolase); Smith et al. (1986) Biochem. Soc. Trans. 14:583–584 (acyl-ACP thioesterase II); 5,559,220 (acetyl Coenzyme A carboxylase); WO98/05758 (acetyl-CoA carboxylase); and the like. See also, U.S. Pat. Nos. 5,411,879; 5,455,167; 5,512,482; 5,344,771; and 5,679,881. Such disclosures are herein incorporated by reference.

For the production of carotenoids, the second gene may correspond to a coding sequence for an enzyme in the carotenoid pathway. Such second genes may be utilized to shunt the acetyl-CoA into carotenoid biosynthesis. In this manner, an increase in the biosynthetic activity of the carotenoid pathway is seen, and increased production of particular carotenoids such as α- and β-carotene can be produced. As with the production of specialty fatty acids, once the biosynthetic activity has been increased, the pathway can be diverted for the production of specific compounds by using any of the coding sequences or antisense constructs for carotenoid biosynthesis. See, above. This diversion may involve the action of at least a third gene of interest. The third gene encodes an enzyme to force the production of a particular compound or alternatively, can encode a protein to stop the pathway for the accumulation of a particular compound.

To stop the pathway, an antisense RNA can be utilized for the accumulation of a particular compound. Alternatively, homologous plant sequences or partial plant sequences can be used to stop the pathway. For example, for the production of lycopene, an antisense lycopene ε-cyclase and the coding sequence for lycopene β-cyclase (Hugueney et al. (1995) *Plant J.* 8:417–424, Cunningham et al. (1994) *Plant Cell* 6:1107–1121, Scholnik and Bartley (1995) *Plant Physiol.* 108:1343) are utilized.

In this manner, the metabolic pathway of interest can be manipulated for the high production of any particular compound of interest in the pathway. Likewise, the pathway can be manipulated to decrease levels of a particular compound by transformation of antisense DNA sequences that prevent the conversion of the precursor compound into the particular compound being regulated. In the same manner, to increase the biosynthesis of branched-chain amino acids, antisense constructs for fatty acid biosynthesis and carotenoid biosynthesis can be utilized. In this embodiment, the acetyl-CoA is shunted into the production of amino acids or secondary metabolites of interest.

Any means for producing a plant comprising the acetyl-CoA synthetase coding sequence or both the acetyl-CoA synthetase and at least a second gene are encompassed by the present invention. For example, the second (or additional) gene of interest can be used to transform a plant at the same time as the acetyl-CoA synthetase (cotransformation), the second gene can be introduced into a plant that has already been transformed with the acetyl-CoA synthetase, or alternatively, transformed plants, one expressing the acetyl-CoA synthetase and one expressing the second gene, can be crossed to bring the genes together in the same plant. Subsequent crosses or transformations can bring additional sequences together in the plant.

By combining the genes with tissue-specific promoters, the metabolite of interest can be altered in particular tissues of the plant. Thus, fatty acid or carotenoid levels in the seed, including embryos and endosperm, can be altered by the use of seed-specific promoters or transcription initiation regions. In addition, other promoters associated with storage proteins or involved in fatty acid biosynthesis may be used.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); EA9; acyl carrier protein; and celA (cellulose synthase) (see the copending application entitled "Seed-Preferred Promoters," U.S. patent application Ser. No. 60/097,233, filed Aug. 20, 1998, herein incorporated by reference). Gama-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc.

Nucleic acid sequences encoding acetyl-CoA synthetase have been isolated from other organisms. It is recognized that other known acetyl-CoA synthetase sequences may be used in the methods of the invention and include, but are not limited to, those described in Shin et al. (1977) *FEMS Microbiol. Lett.* 146:103–108; Garre et al. (1994) *Mol. Gen. Genet.* 244:278–286; and De Virgilio et al. (1992) *Yeast* 8:1043–1051.

The maize sequences can be used to isolate other nucleic acid sequences encoding acetyl-CoA synthetase from other plants. The entire nucleotide sequences as well as fragments or variants thereof may be used in the method of the invention.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence catalyzes the formation of acetyl-CoA. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of an acetyl-CoA synthetase nucleotide sequence that encodes a biologically active portion of an acetyl-CoA synthetase protein of the invention will encode at least 20, 25, 30, 50, 100, 150, 200, 250, 300, 350, 400, 450, 500, 550, 600 contiguous amino acids, or up to the total number of amino acids present in a full-length acetyl-CoA synthetase protein of the invention (for example, 632 amino acids for both SEQ ID NOS: 2 and 4). Fragments of an acetyl-CoA synthetase nucleotide sequence that are useful as hybridization probes for PCR primers generally need not encode a biologically active portion of an acetyl-CoA synthetase protein.

Thus, a fragment of an acetyl-CoA synthetase nucleotide sequence may encode a biologically active portion of an acetyl-CoA synthetase protein, or it may be a fragment that can be used as a hybridization probe or PCR primer using methods disclosed below. A biologically active portion of an acetyl-CoA synthetase protein can be prepared by isolating a portion of one of the acetyl-CoA synthetase nucleotide sequences of the invention, expressing the encoded portion of the acetyl-CoA synthetase protein (e.g., by recombinant expression in vitro), and assessing the activity of the encoded portion of the acetyl-CoA synthetase protein. Nucleic acid molecules that are fragments of an acetyl-CoA synthetase nucleotide sequence comprise at least 16, 20, 50, 75, 100, 150, 200, 250, 300, 350, 400, 500, 600, 700, 800, 900, 1,000, 1,100, 1,200, 1,300, 1,400, 1,500, 1,600, 1,700, 1,800, 1,900, 2,000 nucleotides, or up to the number of nucleotides present in a full-length acetyl-CoA synthetase nucleotide sequence disclosed herein (for example, 2,007 and 2,005 nucleotides for SEQ ID NOS: 1 and 3, respectively).

By "variants" is intended substantially similar sequences. For nucleotide sequences, conservative variants include those sequences that, because of the degeneracy of the genetic code, encode the amino acid sequence of one of the acetyl-CoA synthetase polypeptides of the invention. Naturally occurring variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a acetyl-CoA synthetase protein of the invention. Generally, nucleotide sequence variants of the invention will have at least 40%, 50%, 60%, 70%, generally, 80%, preferably 85%, 90%, up to 95%, 98% sequence identity to its respective native nucleotide sequence.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation.

The proteins of the invention may be altered in various ways including amino acid substitutions, deletions, truncations, and insertions. Methods for such manipulations are generally known in the art. For example, amino acid sequence variants of the acetyl-CoA synthetase proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired ability to catalyzes the formation of acetyl-CoA. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assaying for the altered biosynthesis of a metabolite of interest.

Variant nucleotide sequences and proteins also encompass sequences and proteins derived from a mutagenic and recombinogenic procedure such as DNA shuffling. With such a procedure, one or more different acetyl-CoA synthetase coding sequences can be manipulated to create a new acetyl-CoA synthetase possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the acetyl-CoA synthetase nucleic acid sequence of the invention and other known acetyl-CoA synthetase nucleotide sequences to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The nucleotide sequences of the invention can be used to isolate corresponding sequences from other organisms, particularly other plants, and more particularly other monocots. In this manner, methods such as PCR, hybridization, and the like can be used to identify such sequences based on their sequence homology to the sequences set forth herein. Sequences isolated based on their sequence identity to the entire sequences set forth herein or to fragments thereof are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the acetyl-CoA synthetase sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire acetyl-CoA synthetase sequence disclosed herein, or one or more portions thereof, may be used as a probe capable of specifically hybridizing to corresponding acetyl-CoA synthetase sequences and messenger RNAs. To achieve specific hybridization under a variety of conditions, such probes include sequences that are unique among acetyl-CoA synthetase sequences and are preferably at least about 10 nucleotides in length, and most preferably at least about 20 nucleotides in length. Such probes may be used to amplify corresponding acetyl-CoA synthetase sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m=81.5°\ C.+16.6(\log M)+0.41(\%GC)-0.61(\%\ form)-500/L$; where M is the molarity of monovalent cations, %GC is the percentage of guanosine and cytosine nucleotides in the DNA, % form is the percentage of formamide in the hybridization solution, and L is the length of the hybrid in base pairs. The $T_m$ the temperature (under defined ionic strength and pH) at which 50% of a complementary target sequence hybridizes to a perfectly matched probe. $T_m$ is reduced by about 1 ° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes,* Part I, Chapter 2 (Elsevier, N.Y.); and Ausubel et al., eds. (1995) *Current Protocols in Molecular Biology,* Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

In general, sequences that encode for a acetyl-CoA synthetase protein and hybridize to the acetyl-CoA synthetase sequences disclosed herein will be at least 40% to 50% homologous, about 60% to 70% homologous, and even about 80%, 85%, 90%, 95% to 98% homologous or more with the disclosed sequences. That is, the sequence similarity of sequences may range, sharing at least about 40% to 50%, about 60% to 70%, and even about 80%, 85%, 90%, 95% to 98% sequence similarity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the local homology algorithm of Smith et al. (1981) *Adv. Appl. Math.* 2:482; by the homology alignment algorithm of Needleman et al. (1970) *J. Mol. Biol.* 48:443; by the search for similarity method of Pearson et al. (1988) *Proc. Natl. Acad. Sci.* 85:2444; by computerized implementations of these algorithms, including, but not limited to: CLUSTAL in the PC/Gene program by Intelligenetics, Mountain View, California; GAP, BESTFIT, BLAST, FASTA, and TFASTA in the Wisconsin Genetics Software Package, Genetics Computer Group (GCG), 575 Science Drive, Madison, Wis., USA; the CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *Computer Applications in the Biosciences* 8:155–65, and Person et al. (1994) *Meth. Mol. Biol.* 24:307–331; preferred computer alignment methods also include the BLASTP, BLASTN, and BLASTX algorithms (see Altschul et al. (1990) *J. Mol. Biol.* 215:403–410). Alignment is also often performed by inspection and manual alignment. The alignments are performed using the default parameters of the sequence alignment programs.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties. (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

For the most part, the nucleotide sequences of interest of the present invention will be targeted to the chloroplast for expression to prevent systemic expression of the nucleic acid sequence which could result in morphological deformities. In this manner, where the gene of interest is not directly inserted into the chloroplast, the expression cassette will additionally contain a nucleic acid encoding a transit peptide to direct the gene of interest to the chloroplasts. Such transit peptides are known in the art. See, for example, Von Heijne et al. (1991) *Plant Mol. Biol. Rep.* 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res Commun.* 196:1414–1421; and, Shah et al. (1986) *Science* 233:478–481. Plant carotenoid and fatty acid biosynthesis genes useful in the invention may utilize native or heterologous transit peptides.

Chloroplast targeting sequences are known in the art and include the chloroplast small subunit of ribulose-1,5-bisphosphate carboxylase (Rubisco), (de Castro Silva Filho et al. (1996) *Plant Mol. Biol.* 30:769–780; Schnell, et al. (1991) *J. Biol. Chem.* 266(5):3335–3342); 5-(enolpyruvyl) shikimate-3-phosphate synthase (EPSPS) (Archer et al. (1990) *J. Bioenerg. Biomemb.* 22(6):789–810); tryptophan synthase (Zhao et al. (1995) *J. Biol. Chem.* 270(11) :6081–6087); plastocyanin (Lawrence et al. (1997) *J. Biol. Chem.* 272(33):20357–20363); chorismate synthase (Schmidt et al. (1993) *J. Biol. Chem.* 268(36) :27477–27457); and the light harvesting chlorophyll a/b binding protein (LHBP) (Lamppa et al. (1988) *J. Biol. Chem.* 263:14996–14999). See also Von Heijne et al. (1991) *Plant Mol. Biol. Rep.* 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res Commun.* 196:1414–1421; and Shah et al. (1986) *Science* 233:478–481.

Methods for transformation of chloroplasts are known in the art. See, for example, Svab et al. (1990) *Proc. Natl. Acad. Sci. USA* 87:8526–8530; Svab and Maliga (1993) *Proc. Natl. Acad. Sci. USA* 90:913–917; Staub and Maliga (1993) *Embo J.* 12:601–606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-specific expression of a nuclear-encoded and plastid-directed RNA polymerase. Such a system has been reported in McBride et al. (1994) *Proc. Natl. Acad. Sci. USA* 91:7301–7305.

The sequences of the invention can be introduced into any plant. The sequences to be introduced may be used in expression cassettes for expression in any plant of interest where expression in the plant is necessary for transcription.

Of particular interest are plants where the seed is produced in high amounts, or the seed or a seed part is edible. Seeds of interest include the oil seeds, such as seeds from Brassica, cotton, soybean, safflower, sunflower, coconut, palm, etc.; grain seeds such as wheat, barley, rice, corn, etc.; other seeds including oats, pumpkin, squash, poppy, sesame, peanut, peas, beans, cocoa, coffee, etc.; and tree nuts such as walnuts, pecans, almonds, etc.

"Operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

Nucleotide sequences of the invention are provided in expression cassettes for expression in the plant of interest. The cassette will include 5' and 3' regulatory sequences operably linked to the sequence of interest. The cassette may additionally contain at least one additional sequence to be cotransformed into the organism. Alternatively, the additional sequence(s) can be provided on another expression cassette.

The transcriptional initiation region, the promoter, may be native or analogous or foreign or heterologous to the plant host. Additionally, the promoter may be the natural sequence or alternatively a synthetic sequence. By foreign is intended that the transcriptional initiation region is not found in the native plant into which the transcriptional initiation region is introduced. As used herein a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of acetyl-CoA synthetase in the plant or plant cell. Thus, the phenotype of the plant or plant cell is altered.

The transcriptional cassette will include in the 5'-to-3' direction of transcription, a transcriptional and translational initiation region, a acetyl-CoA synthetase sequence, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell.* 2:1261–1272; Munroe et al. (1990) *Gene* 91:151–158; Ballas et al. (1989) *Nucleic Acids Res.* 17:7891–7903; Joshi et al. (1987) *Nucleic Acids Res.* 15:9627–9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA,* ed. Cech (Liss, N.Y.), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) in *The Operon,* pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology,* Vol. 78 ( Springer-Verlag, Berlin); Gill et al. (1988) *Nature* 334:721–724. Such disclosures are herein incorporated by reference.

The above list of selectable marker genes is not meant to be limiting. Any selectable marker gene can be used in the present invention.

Specific embodiments of the present invention will require that antisense constructions of nucleotide sequences of interest be constructed. The antisense constructs will contain at least a portion of the messenger RNA (mRNA) for the nucleotide sequences. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence similarity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

The sequences of the present invention can be used to transform or transfect any plant. In this manner, genetically modified plants, plant cells, plant tissue, seed, and the like can be obtained. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods,* ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P: 175–182 (soybean); Singh et al. (1998) *Theor. Appl. Genet.* 96:319–324 (soybean); Datta et al. (1990) *Biotechnology*

8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature (London)* 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The modified plant may be grown into plants in accordance with conventional ways. See, for example, McCormick et al. (1986) *Plant Cell. Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The following examples are offered by way of illustration and not by way of limitation.

Experimental

EXAMPLE 1
Incorporation of Acetyl-CoA Synthetase DNA Sequences into Expression Vectors The full-length acetyl-CoA synthetase clone was "captured" from a maize leaf library. The T3 priming site present in every clone was used to serve as an anchor primer for PCR reactions. Gene specific primers were designed and primary and secondary PCR reactions were performed. These reactions resulted in a ladder of products of increasing molecular weight that upon characterization represented various states of clone truncation. The product that exhibited the greatest molecular weight resulted in the addition of 450 bp of sequence to the information in the sequence database. This information was used to compile a full-length clone. Additional sequence analysis and database comparisons will be conducted.

The 5' end of HGS clone CBIFK38 was obtained via library RACE. This information was used with the partial sequence data from above to compile a putative full-length contig. Additional sequence analysis and database comparisons were conducted to determine a putative protein translation initiation site. There were several ATGs present in the sequence that could serve as initiation codons for protein translation with no clear consensus as to the correct one. Additional characterization of the clones obtained from the PCR product exhibiting the greatest molecular weight revealed that in addition to cloning the 5' end of CBIFK38, the 5' end of another Acetyl-CoA synthetase gene (CDPFM42) was also cloned in a single PCR reaction. This information provided a direct comparison to clone CBIFK38 and allowed for a determination of the start of protein translation. The two clones appear to share a very high degree of identity based on 5' protein sequence. These data were used to design 5' and 3' primers specific for each gene. PCR was used to generate products of the expected molecular weight using a maize leaf cDNA library as background. These clones should represent the complete open reading frames of CBIFK38 and CDPFM42. These products were cloned into the TA cloning vector pCRII-TOPO.

Primer pairs were designed for the clones representing the complete open reading frames of CBIFK38 and CDPFM42 to allow both stands to be completely sequenced.

Multiple sequencing runs have been assembled into full length contigs for HGS clones CBIFK38 and CDPFM42. The contigs have also been completely edited to give two final consensus sequences. These data were analyzed to decide upon a cloning strategy for insertion of the open reading frames into a pET expression vector. Appropriate primers have been designed for inserting both genes as Nco I/Xho I fragments into pET 15b. Vector construction of two ACoAS::pET 15b expression constructs has been completed for HGS clones CBIFK38 and CDPFM42. Clones have been transformed into the expression host BL21(DE3)pLysS. Induction and expression studies are pending.

EXAMPLE 2
Transformation and Regeneration of Maize Callus

Immature maize embryos from greenhouse donor plants are bombarded with a plasmid containing acetyl-CoA synthetase operably linked to a Ubiquitin promoter and containing the PinII terminator sequences (FIG. 1). In addition, this plasmid also contains the selectable marker gene PAT (Wohlleben et al. (1988) *Gene* 70:25–37) that confers resistance to the herbicide Bialaphos. Transformation is performed as follows. All media recipes are in the Appendix.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the acetyl-CoA synthetase operably linked to a Ubiquitin promoter and containing the PinII terminator sequences is generated. This plasmid also contains the selectable marker gene PAT. The plasmid is precipitated onto 1.1 µm (average diameter) tungsten pellets using a $CaCl_2$ precipitation procedure as follows:

100 µl prepared tungsten particles in water
    10 µl (1 µg) DNA in TrisEDTA buffer (1 µg total)
    100 µl 2.5 M $CaCl_2$
    10 µl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

Particle Gun Treatment

The sample plates are bombarded at level #4 in particle gun #HE34–1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for expression of the acetyl-CoA synthetase gene of interest.

APPENDIX

272 V

| Ingredient | Amount | Unit |
| --- | --- | --- |
| D-I H$_2$O | 950.000 | Ml |
| MS Salts (GIBCO 11117-074) | 4.300 | G |
| Myo-Inositol | 0.100 | G |
| MS Vitamins Stock Solution ## | 5.000 | Ml |
| Sucrose | 40.000 | G |
| Bacto-Agar @ | 6.000 | G |

Directions
@=Add after bringing up to volume
Dissolve ingredients in polished D-I H$_2$O in sequence
Adjust to pH 5.6
Bring up to volume with polished D-I H$_2$O after adjusting pH
Sterilize and cool to 60° C.
=Dissolve 0.100 g of Nicotinic Acid; 0.020 g of Thiamine.HCL; 0.100 g of
Pyridoxine.HCL; and 0.400 g of Glycine in 875.00 ml of polished D-I H$_2$O in sequence.
Bring up to volume with polished D-I H$_2$O. Make in 400 ml portions. Thiamine.HCL & Pyridoxine.HCL are in Dark Desiccator. Store for one month, unless contamination or precipitation occurs, then make fresh stock.
Total Volume (L)=1.00

288 J

| Ingredient | Amount | Unit |
| --- | --- | --- |
| D-I H$_2$O | 950.000 | Ml |
| MS Salts | 4.300 | g |
| Myo-Inositol | 0.100 | g |
| MS Vitamins Stock Solution ## | 5.000 | ml |
| Zeatin .5 mg/ml | 1.000 | ml |
| Sucrose | 60.000 | g |
| Gelrite @ | 3.000 | g |
| Indoleacetic Acid 0.5 mg/ml # | 2.000 | ml |
| 0.1 mM Abscisic Acid | 1.000 | ml |
| Bialaphos 1 mg/ml # | 3.000 | ml |

Directions
@=Add after bringing up to volume
Dissolve ingredients in polished D-I H$_2$O in sequence
Adjust to pH 5.6
Bring up to volume with polished D-I H$_2$O after adjusting pH
Sterilize and cool to 60° C.
Add 3.5 g/L of Gelrite for cell biology.
=Dissolve 0.100 g of Nicotinic Acid; 0.020 g of Thiamine.HCL; 0.100 g of
Pyridoxine.HCL; and 0.400 g of Glycine in 875.00 ml of polished D-I H$_2$O in sequence.
Bring up to volume with polished D-I H$_2$O. Make in 400 ml portions. Thiamine.HCL & Pyridoxine.HCL are in Dark Desiccator. Store for one month, unless contamination or precipitation occurs, then make fresh stock.
Total Volume (L)=1.00

560 R

| Ingredient | Amount | Unit |
| --- | --- | --- |
| D-I Water, Filtered | 950.000 | ml |
| CHU (N6) Basal Salts (SIGMA C-1416) | 4.000 | g |
| Eriksson's Vitamin Mix (1000X SIGMA-1511) | 1.000 | ml |
| Thiamine.HCL 0.4 mg/ml | 1.250 | ml |
| Sucrose | 30.000 | g |
| 2,4-D 0.5 mg/ml | 4.000 | ml |
| Gelrite @ | 3.000 | g |
| Silver Nitrate 2 mg/ml # | 0.425 | ml |
| Bialaphos 1 mg/ml # | 3.000 | ml |

Directions
@=Add after bringing up to volume
=Add after sterilizing and cooling to temp.
Dissolve ingredients in D-I H$_2$O in sequence
Adjust to pH 5.8 with KOH
Bring up to volume with D-I H$_2$O
Sterilize and cool to room temp.
Total Volume (L)=1.00

560 Y

| Ingredient | Amount | Unit |
| --- | --- | --- |
| D-I Water, Filtered | 950.000 | ml |
| CHU (N6) Basal Salts (SIGMA C-1416) | 4.000 | g |
| Eriksson's Vitamin Mix (1000X SIGMA-1511) | 1.000 | ml |
| Thiamine.HCL 0.4 mg/ml | 1.250 | ml |
| Sucrose | 120.000 | g |
| 2.4-D 0.5 mg/ml | 2.000 | ml |
| L-Proline | 2.880 | g |
| Gelrite @ | 2.000 | g |
| Silver Nitrate 2 mg/ml # | 4.250 | ml |

Directions
@=Add after bringing up to volume
=Add after sterilizing and cooling to temp.
Dissolve ingredients in D-I H$_2$O in sequence
Adjust to pH 5.8 with KOH Bring up to volume with D-I H$_2$O
Sterilize and cool to room temp.
 Autoclave less time because of increased sucrose
Total Volume (L)=1.00

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid comprising a nucleotide sequence of a *Zea mays* acetyl-CoA synthetase set forth in one of SEQ ID NOS: 1 or 3.

2. An isolated nucleic acid comprising a nucleotide sequence encoding a *Zea mays* acetyl-CoA synthetase set forth in one of SEQ ID NOS: 2 or 4.

3. An isolated nucleic acid encoding acetyl-CoA synthetase having at least 90% identity to one of SEQ ID NOS: 1 or 3 as determined by the GAP algorithm under default parameters.

4. A transformed plant, the plant having stably incorporated into its genome an expression cassette, wherein the expression cassette comprises a promoter operably linked to a nucleotide sequence encoding acetyl-CoA synthetase wherein the nucleotide sequence has at least 90% identity to one of SEQ ID NOS: 1 or 3 as determined by the GAP algorithm under default parameters.

5. A seed of the plant of claim 4.

6. The transformed plant of claim 4 wherein the nucleotide sequence comprises one of SEQ ID NOS: 1 or 3.

7. A transformed plant cell, the plant having stably incorporated into its genome an expression cassette, wherein the expression cassette comprises a promoter operably linked to a nucleotide sequence encoding acetyl-CoA synthetase wherein the nucleotide sequence has at least 90% identity to one of SEQ ID NOS: 1 or 3 as determined by the GAP algorithm under default parameters.

8. The transformed plant cell of claim 7, wherein the nucleotide sequence comprises one of SEQ ID NOS: 1 or 3.

* * * * *

SEQUENCE LISTING

<160> NUMBER OF SEQ ID NOS: 4

<210> SEQ ID NO 1
<211> LENGTH: 2007
<212> TYPE: DNA
<213> ORGANISM: Zea mays
<220> FEATURE:
<221> NAME/KEY: CDS
<222> LOCATION: (79)...(1974)

<400> SEQUENCE: 1

```
gaggagaacg acctcatcgt ccccagcccc gagttctctg ccagcgccct cgtctcttct        60
ccgaaacagt atcgcgag atg tat gag agg tcc att aag gac ccg gcc ggg        111
                    Met Tyr Glu Arg Ser Ile Lys Asp Pro Ala Gly
                     1               5                  10 ttc tgg tcg gag att gcc gag acc ttt tac tgg aag gag aag tgg aac        159
Phe Trp Ser Glu Ile Ala Glu Thr Phe Tyr Trp Lys Glu Lys Trp Asn
             15                  20                  25 ccc gcc gag gtc tgc tcg gag aac ctc gat gtc acc aag gga ccc gtc        207
Pro Ala Glu Val Cys Ser Glu Asn Leu Asp Val Thr Lys Gly Pro Val
         30                  35                  40 cag atc aac tgg ttc aag gga ggg aaa acc aac ata tgt tac aac gct        255
Gln Ile Asn Trp Phe Lys Gly Gly Lys Thr Asn Ile Cys Tyr Asn Ala
     45                  50                  55 gtt gac cgc aac atc gag tct ggc aat ggc gac aag gtt gca atg tac        303
Val Asp Arg Asn Ile Glu Ser Gly Asn Gly Asp Lys Val Ala Met Tyr
 60                  65                  70                  75 tgg gag ggt aat gag ccc ggt cag gat ggg aag ctt acc tat tcc gag        351
Trp Glu Gly Asn Glu Pro Gly Gln Asp Gly Lys Leu Thr Tyr Ser Glu
                 80                  85                  90 ctc ctg gag aag gtt tgc cag ctt gca aat tac ttg aag agc ctt ggt        399
Leu Leu Glu Lys Val Cys Gln Leu Ala Asn Tyr Leu Lys Ser Leu Gly
             95                 100                 105 gtc ggc aag ggt gat gct gtt att ata tac cta cca atg ttg ctg gag        447
Val Gly Lys Gly Asp Ala Val Ile Ile Tyr Leu Pro Met Leu Leu Glu
        110                 115                 120 ctt ccc att gcc atg ctt gcc tgt gcc cgc att ggt gcc gtt cac tcg        495
Leu Pro Ile Ala Met Leu Ala Cys Ala Arg Ile Gly Ala Val His Ser
    125                 130                 135 gtt gtg ttt gct ggc ttc tca gca gat tcg cta gct caa agg att gtc        543
Val Val Phe Ala Gly Phe Ser Ala Asp Ser Leu Ala Gln Arg Ile Val
140                 145                 150                 155 gat tgc aag cct aag ctt gtc atc acg tgc aat gct gtg aag cgg gga        591
Asp Cys Lys Pro Lys Leu Val Ile Thr Cys Asn Ala Val Lys Arg Gly
                160                 165                 170 gtc aag ccc atc ttt ctc aaa gat ata gtg gat gca gct ttg gtt gaa        639
Val Lys Pro Ile Phe Leu Lys Asp Ile Val Asp Ala Ala Leu Val Glu
            175                 180                 185 agt gag aag aat gga gtc tct gta ggt ctc tgt ttg acg tat gaa aac        687
Ser Glu Lys Asn Gly Val Ser Val Gly Leu Cys Leu Thr Tyr Glu Asn
        190                 195                 200
```

```
cag tca gcc atg aag agg gaa aac aca aaa tgg caa gca gaa agg gat      735
Gln Ser Ala Met Lys Arg Glu Asn Thr Lys Trp Gln Ala Glu Arg Asp
        205                 210                 215 gtt tgg tgg cag gac gtt gtc aca aaa ttt cca acc aaa tgt gat gtg      783
Val Trp Trp Gln Asp Val Val Thr Lys Phe Pro Thr Lys Cys Asp Val
220                 225                 230                 235 gag tgg gtg gat gca gag gat cca ttg ttc ctt ttg tac aca agt ggc      831
Glu Trp Val Asp Ala Glu Asp Pro Leu Phe Leu Leu Tyr Thr Ser Gly
                    240                 245                 250 agc aca ggg aag cca aag ggt gta ctg cat act tct ggg ggc tac atg      879
Ser Thr Gly Lys Pro Lys Gly Val Leu His Thr Ser Gly Gly Tyr Met
                255                 260                 265 gtg tac act gca aca aca ttt aag tac gca ttt gac tac aag cca act      927
Val Tyr Thr Ala Thr Thr Phe Lys Tyr Ala Phe Asp Tyr Lys Pro Thr
            270                 275                 280 gac ata tac tgg tgc act gca gac tgt ggc tgg att act gga cat agt      975
Asp Ile Tyr Trp Cys Thr Ala Asp Cys Gly Trp Ile Thr Gly His Ser
        285                 290                 295 tat gta aca tat ggt cct ctc ctg aat ggt gct acg gtt ctc gtt ttt     1023
Tyr Val Thr Tyr Gly Pro Leu Leu Asn Gly Ala Thr Val Leu Val Phe
300                 305                 310                 315 gaa ggg acg ccg aac tac cct gat tcg ggc cga tgc tgg gat att gtg     1071
Glu Gly Thr Pro Asn Tyr Pro Asp Ser Gly Arg Cys Trp Asp Ile Val
                    320                 325                 330 gac aag tac aat gtg aca ata ttt tat act gcc cca act ctt gtt cgt     1119
Asp Lys Tyr Asn Val Thr Ile Phe Tyr Thr Ala Pro Thr Leu Val Arg
                335                 340                 345 tca ctc atg cgt gat ggc act gag tat gtt aca cgt tac tct cga aag     1167
Ser Leu Met Arg Asp Gly Thr Glu Tyr Val Thr Arg Tyr Ser Arg Lys
            350                 355                 360 tct ctc cga gtc ctg gga agt gtt ggt gag cca atc aat cct agt gca     1215
Ser Leu Arg Val Leu Gly Ser Val Gly Glu Pro Ile Asn Pro Ser Ala
        365                 370                 375 tgg aga tgg ttc tac aat act gtt ggg gat tcc cgg tgc cct ata tca     1263
Trp Arg Trp Phe Tyr Asn Thr Val Gly Asp Ser Arg Cys Pro Ile Ser
380                 385                 390                 395 gac acc tgg tgg caa act gaa act ggc ggt ttc atg atc acc cct ttg     1311
Asp Thr Trp Trp Gln Thr Glu Thr Gly Gly Phe Met Ile Thr Pro Leu
                    400                 405                 410 cct ggc gcc tgg cct caa aaa cca ggt tct gca acc ttt cct ttc ttt     1359
Pro Gly Ala Trp Pro Gln Lys Pro Gly Ser Ala Thr Phe Pro Phe Phe
                415                 420                 425 ggt gtt cag ccg gtc att gtt gac gag aaa ggg caa gag att gaa ggg     1407
Gly Val Gln Pro Val Ile Val Asp Glu Lys Gly Gln Glu Ile Glu Gly
            430                 435                 440 gaa tgt agt gga tat ctt tgc ata aag aaa tca tgg cct ggg gct ttc     1455
Glu Cys Ser Gly Tyr Leu Cys Ile Lys Lys Ser Trp Pro Gly Ala Phe
        445                 450                 455 cgg act ctg tat gga gat cat gag aga tac gag acc acg tac ttc aaa     1503
Arg Thr Leu Tyr Gly Asp His Glu Arg Tyr Glu Thr Thr Tyr Phe Lys
460                 465                 470                 475 cca ttt gct ggg tac tat ttc act ggt gat ggt gca gca gac aaa         1551
Pro Phe Ala Gly Tyr Tyr Phe Thr Gly Asp Gly Cys Ser Arg Asp Lys
                    480                 485                 490 gat ggt tac cac tgg ctg act gga aga gta gat gat gtc atc aat gtc     1599
Asp Gly Tyr His Trp Leu Thr Gly Arg Val Asp Asp Val Ile Asn Val
                495                 500                 505 agt gga cac cga atc ggc aca gca gag gtt gag tca gct tta gtg tca     1647
Ser Gly His Arg Ile Gly Thr Ala Glu Val Glu Ser Ala Leu Val Ser
```

-continued

```
              510                 515                 520
cat cca cag tgt gca gag gct gct gtt gtt ggt gtt gag cat gag gtc    1695
His Pro Gln Cys Ala Glu Ala Ala Val Val Gly Val Glu His Glu Val
        525                 530                 535 aaa ggt caa gga att tat gct ttt gta act ttg gtg gat ggt gtt ccg    1743
Lys Gly Gln Gly Ile Tyr Ala Phe Val Thr Leu Val Asp Gly Val Pro
540                 545                 550                 555 tat agt gag gaa cta cga aaa agc ctc ata atg aca gtg cgc aac cag    1791
Tyr Ser Glu Glu Leu Arg Lys Ser Leu Ile Met Thr Val Arg Asn Gln
                560                 565                 570 att ggg gca ttt gca gct cct gac aag atc cac tgg gca ccg gga ctt    1839
Ile Gly Ala Phe Ala Ala Pro Asp Lys Ile His Trp Ala Pro Gly Leu
            575                 580                 585 cct aaa acc cgg agt ggc aag atc atg cga agg att ttg cgc aag att    1887
Pro Lys Thr Arg Ser Gly Lys Ile Met Arg Arg Ile Leu Arg Lys Ile
        590                 595                 600 gct gca cgg caa ctg gat gaa ctt ggg gac ata agc acc ctc gct gaa    1935
Ala Ala Arg Gln Leu Asp Glu Leu Gly Asp Ile Ser Thr Leu Ala Glu
    605                 610                 615 cct gct gta gtt gac cag ctt att tcg ctc agc aat tgt taggttgcaa    1984
Pro Ala Val Val Asp Gln Leu Ile Ser Leu Ser Asn Cys
620                 625                 630 cgtaattgga tggtggatac atc                                          2007
```

<210> SEQ ID NO 2
<211> LENGTH: 632
<212> TYPE: PRT
<213> ORGANISM: Zea mays

<400> SEQUENCE: 2

```
Met Tyr Glu Arg Ser Ile Lys Asp Pro Ala Gly Phe Trp Ser Glu Ile
1               5                   10                  15

Ala Glu Thr Phe Tyr Trp Lys Glu Lys Trp Asn Pro Ala Glu Val Cys
                20                  25                  30

Ser Glu Asn Leu Asp Val Thr Lys Gly Pro Val Gln Ile Asn Trp Phe
            35                  40                  45

Lys Gly Gly Lys Thr Asn Ile Cys Tyr Asn Ala Val Asp Arg Asn Ile
        50                  55                  60

Glu Ser Gly Asn Gly Asp Lys Val Ala Met Tyr Trp Glu Gly Asn Glu
65                  70                  75                  80

Pro Gly Gln Asp Gly Lys Leu Thr Tyr Ser Glu Leu Leu Glu Lys Val
                85                  90                  95

Cys Gln Leu Ala Asn Tyr Leu Lys Ser Leu Gly Val Gly Lys Gly Asp
                100                 105                 110

Ala Val Ile Ile Tyr Leu Pro Met Leu Leu Glu Leu Pro Ile Ala Met
            115                 120                 125

Leu Ala Cys Ala Arg Ile Gly Ala Val His Ser Val Phe Ala Gly
        130                 135                 140

Phe Ser Ala Asp Ser Leu Ala Gln Arg Ile Val Asp Cys Lys Pro Lys
145                 150                 155                 160

Leu Val Ile Thr Cys Asn Ala Val Lys Arg Gly Val Lys Pro Ile Phe
                165                 170                 175

Leu Lys Asp Ile Val Asp Ala Ala Leu Val Glu Ser Glu Lys Asn Gly
                180                 185                 190

Val Ser Val Gly Leu Cys Leu Thr Tyr Glu Asn Gln Ser Ala Met Lys
            195                 200                 205
```

-continued

```
Arg Glu Asn Thr Lys Trp Gln Ala Glu Arg Asp Val Trp Trp Gln Asp
    210                 215                 220
Val Val Thr Lys Phe Pro Thr Lys Cys Asp Val Glu Trp Val Asp Ala
225                 230                 235                 240
Glu Asp Pro Leu Phe Leu Leu Tyr Thr Ser Gly Ser Thr Gly Lys Pro
                245                 250                 255
Lys Gly Val Leu His Thr Ser Gly Gly Tyr Met Val Tyr Thr Ala Thr
                260                 265                 270
Thr Phe Lys Tyr Ala Phe Asp Tyr Lys Pro Thr Asp Ile Tyr Trp Cys
        275                 280                 285
Thr Ala Asp Cys Gly Trp Ile Thr Gly His Ser Tyr Val Thr Tyr Gly
    290                 295                 300
Pro Leu Leu Asn Gly Ala Thr Val Leu Val Phe Glu Gly Thr Pro Asn
305                 310                 315                 320
Tyr Pro Asp Ser Gly Arg Cys Trp Asp Ile Val Asp Lys Tyr Asn Val
                325                 330                 335
Thr Ile Phe Tyr Thr Ala Pro Thr Leu Val Arg Ser Leu Met Arg Asp
                340                 345                 350
Gly Thr Glu Tyr Val Thr Arg Tyr Ser Arg Lys Ser Leu Arg Val Leu
        355                 360                 365
Gly Ser Val Gly Glu Pro Ile Asn Pro Ser Ala Trp Arg Trp Phe Tyr
    370                 375                 380
Asn Thr Val Gly Asp Ser Arg Cys Pro Ile Ser Asp Thr Trp Trp Gln
385                 390                 395                 400
Thr Glu Thr Gly Gly Phe Met Ile Thr Pro Leu Pro Gly Ala Trp Pro
                405                 410                 415
Gln Lys Pro Gly Ser Ala Thr Phe Pro Phe Gly Val Gln Pro Val
                420                 425                 430
Ile Val Asp Glu Lys Gly Gln Glu Ile Glu Gly Glu Cys Ser Gly Tyr
        435                 440                 445
Leu Cys Ile Lys Lys Ser Trp Pro Gly Ala Phe Arg Thr Leu Tyr Gly
    450                 455                 460
Asp His Glu Arg Tyr Glu Thr Thr Tyr Phe Lys Pro Phe Ala Gly Tyr
465                 470                 475                 480
Tyr Phe Thr Gly Asp Gly Cys Ser Arg Asp Lys Asp Gly Tyr His Trp
                485                 490                 495
Leu Thr Gly Arg Val Asp Asp Val Ile Asn Val Ser Gly His Arg Ile
                500                 505                 510
Gly Thr Ala Glu Val Glu Ser Ala Leu Val Ser His Pro Gln Cys Ala
        515                 520                 525
Glu Ala Ala Val Val Gly Val Glu His Glu Val Lys Gly Gln Gly Ile
    530                 535                 540
Tyr Ala Phe Val Thr Leu Val Asp Gly Val Pro Tyr Ser Glu Glu Leu
545                 550                 555                 560
Arg Lys Ser Leu Ile Met Thr Val Arg Asn Gln Ile Gly Ala Phe Ala
                565                 570                 575
Ala Pro Asp Lys Ile His Trp Ala Pro Gly Leu Pro Lys Thr Arg Ser
                580                 585                 590
Gly Lys Ile Met Arg Arg Ile Leu Arg Lys Ile Ala Ala Arg Gln Leu
        595                 600                 605
Asp Glu Leu Gly Asp Ile Ser Thr Leu Ala Glu Pro Ala Val Val Asp
    610                 615                 620
Gln Leu Ile Ser Leu Ser Asn Cys
```

```
<210> SEQ ID NO 3
<211> LENGTH: 2005
<212> TYPE: DNA
<213> ORGANISM: Zea mays
<220> FEATURE:
<221> NAME/KEY: CDS
<222> LOCATION: (77)...(1972)

<400> SEQUENCE: 3
ccccggcatc ctcgtccacc ccagcgccga cttcgccgcc caggcgctcg tctcgtccac      60
gcaacagtac cgagat atg tac caa aag tcg atc gac gac cca gct ggt ttc    112
               Met Tyr Gln Lys Ser Ile Asp Asp Pro Ala Gly Phe
                 1               5                  10 tgg tcg gaa atc gca gat gag ttc tac tgg aag cag aag tgg agc cct      160
Trp Ser Glu Ile Ala Asp Glu Phe Tyr Trp Lys Gln Lys Trp Ser Pro
         15                  20                  25 gat aat gtt tgc gct gag aac ctt gac gtg acc aag ggg ccg atc atg      208
Asp Asn Val Cys Ala Glu Asn Leu Asp Val Thr Lys Gly Pro Ile Met
 30                  35                  40 att gaa tgg ttt aag ggg gga aag acc aac ata tgc tac aat gca gtg      256
Ile Glu Trp Phe Lys Gly Gly Lys Thr Asn Ile Cys Tyr Asn Ala Val
 45                  50                  55                  60 gac cgc aat gtg gag gca ggg aat ggg gac aag atc gcc atg tac tgg      304
Asp Arg Asn Val Glu Ala Gly Asn Gly Asp Lys Ile Ala Met Tyr Trp
                 65                  70                  75 gag ggg aat gag ccc agt cag gat ggg aag ctc acc tac tct gaa ctg      352
Glu Gly Asn Glu Pro Ser Gln Asp Gly Lys Leu Thr Tyr Ser Glu Leu
         80                  85                  90 ctg gaa aag gtt tgc cag ctg tca aat tac ttg aaa agc gtc ggc gta      400
Leu Glu Lys Val Cys Gln Leu Ser Asn Tyr Leu Lys Ser Val Gly Val
         95                 100                 105 cga aag ggt gat gcc gtg gtg atc tac cta cca atg ttg atg gag ctg      448
Arg Lys Gly Asp Ala Val Val Ile Tyr Leu Pro Met Leu Met Glu Leu
110                 115                 120 ccg att gca atg ctt gct tgt gct cgc att ggt gtt gtt cac tcg gtt      496
Pro Ile Ala Met Leu Ala Cys Ala Arg Ile Gly Val Val His Ser Val
125                 130                 135                 140 gtg ttt gct ggc ttc tca gca gat gca ctg gcc caa cga gtc att gat      544
Val Phe Ala Gly Phe Ser Ala Asp Ala Leu Ala Gln Arg Val Ile Asp
                145                 150                 155 tgc aag cct aag gtt gtt att acc tgc aat gct gtg aaa agg ggg atg      592
Cys Lys Pro Lys Val Val Ile Thr Cys Asn Ala Val Lys Arg Gly Met
                160                 165                 170 aaa atc atc cct ctc aaa gat ata gta gat gca tct ctg gat caa agt      640
Lys Ile Ile Pro Leu Lys Asp Ile Val Asp Ala Ser Leu Asp Gln Ser
                175                 180                 185 gca aag aat gga gtt gat gta ggc att tgc ttg aca tat gaa aat cag      688
Ala Lys Asn Gly Val Asp Val Gly Ile Cys Leu Thr Tyr Glu Asn Gln
190                 195                 200 tcc gct ctg aat aaa gta gac act cga cgg aaa aca gga aga gat gtc      736
Ser Ala Leu Asn Lys Val Asp Thr Arg Arg Lys Thr Gly Arg Asp Val
205                 210                 215                 220 tgg tgg cag gat gtt gtg cct gat ttc cca act aaa tgc gat gtg gaa      784
Trp Trp Gln Asp Val Val Pro Asp Phe Pro Thr Lys Cys Asp Val Glu
                225                 230                 235 tgg gtt gat gca gag gat cca ctg ttt ctt ttg tac aca agt ggc agc      832
Trp Val Asp Ala Glu Asp Pro Leu Phe Leu Leu Tyr Thr Ser Gly Ser
                240                 245                 250
```

-continued

| | |
|---|---|
| aca gga aag cca aag ggt gtg ttg cat aca act ggg gga tat atg gtc<br>Thr Gly Lys Pro Lys Gly Val Leu His Thr Thr Gly Gly Tyr Met Val<br>                255                      260                      265 | 880 |
| tac tct gct aca aca ttt aag cat gca ttt gac tac aaa cca aca gat<br>Tyr Ser Ala Thr Thr Phe Lys His Ala Phe Asp Tyr Lys Pro Thr Asp<br>    270                      275                      280 | 928 |
| ata tac tgg tgc act gca gat tgt ggc tgg att act gga cat agt tat<br>Ile Tyr Trp Cys Thr Ala Asp Cys Gly Trp Ile Thr Gly His Ser Tyr<br>285                      290                      295                      300 | 976 |
| gtg aca tat ggt cca cta ttg aat gga gcc aca gtt ctt gtt ttc gaa<br>Val Thr Tyr Gly Pro Leu Leu Asn Gly Ala Thr Val Leu Val Phe Glu<br>                305                      310                      315 | 1024 |
| ggg gcc cca aat tac cct gat cct ggc cgc tgt tgg gac att gtt gat<br>Gly Ala Pro Asn Tyr Pro Asp Pro Gly Arg Cys Trp Asp Ile Val Asp<br>    320                      325                      330 | 1072 |
| aaa tat gga gtg aca ata ttt tat act gca cca aca ctt ata cgc tca<br>Lys Tyr Gly Val Thr Ile Phe Tyr Thr Ala Pro Thr Leu Ile Arg Ser<br>                335                      340                      345 | 1120 |
| ctt atg cgt gat ggt act gag tat gtt gct cgg tac tct cgc aag tct<br>Leu Met Arg Asp Gly Thr Glu Tyr Val Ala Arg Tyr Ser Arg Lys Ser<br>    350                      355                      360 | 1168 |
| ctc cga gta ctt gga agt gtg ggt gag cca atc aac ccc acc gca tgg<br>Leu Arg Val Leu Gly Ser Val Gly Glu Pro Ile Asn Pro Thr Ala Trp<br>365                      370                      375                      380 | 1216 |
| agg tgg ttt tat gat gtt att ggt gac tca cga tgc cca ata tca gat<br>Arg Trp Phe Tyr Asp Val Ile Gly Asp Ser Arg Cys Pro Ile Ser Asp<br>                385                      390                      395 | 1264 |
| act tgg tgg cag act gaa act ggg gga ttc atg atc act cct tta cct<br>Thr Trp Trp Gln Thr Glu Thr Gly Gly Phe Met Ile Thr Pro Leu Pro<br>                    400                      405                      410 | 1312 |
| ggt gct tgg cct caa aag cct gga tcg gca acg ttt cct ttc ttc ggt<br>Gly Ala Trp Pro Gln Lys Pro Gly Ser Ala Thr Phe Pro Phe Phe Gly<br>    415                      420                      425 | 1360 |
| gtg cag cca gtc att gtt gac gag aaa ggt cgg gaa atg gaa gga gaa<br>Val Gln Pro Val Ile Val Asp Glu Lys Gly Arg Glu Met Glu Gly Glu<br>                430                      435                      440 | 1408 |
| tgc agt gga tat ctt tgc ata aag aaa tca tgg cct ggg gct ttc cgg<br>Cys Ser Gly Tyr Leu Cys Ile Lys Lys Ser Trp Pro Gly Ala Phe Arg<br>445                      450                      455                      460 | 1456 |
| act ctg tat gga gat aaa gag aga tat gag acg aca tac ttc aaa cca<br>Thr Leu Tyr Gly Asp Lys Glu Arg Tyr Glu Thr Thr Tyr Phe Lys Pro<br>                    465                      470                      475 | 1504 |
| ttt gct gga tat tat ttc tcg ggc gat ggc tgc agc agg gat aaa gat<br>Phe Ala Gly Tyr Tyr Phe Ser Gly Asp Gly Cys Ser Arg Asp Lys Asp<br>            480                      485                      490 | 1552 |
| ggc tac cac tgg ctg act gga aga gtt gat gat gtt atc aat gtt agt<br>Gly Tyr His Trp Leu Thr Gly Arg Val Asp Asp Val Ile Asn Val Ser<br>                495                      500                      505 | 1600 |
| gga cac cgg att ggg aca gcg gaa gtt gag tct gct ctg gtt tca cat<br>Gly His Arg Ile Gly Thr Ala Glu Val Glu Ser Ala Leu Val Ser His<br>    510                      515                      520 | 1648 |
| cca aaa tgt gct gag gct gct gtt gtt ggt att gat cat gag gtt aaa<br>Pro Lys Cys Ala Glu Ala Ala Val Val Gly Ile Asp His Glu Val Lys<br>525                      530                      535                      540 | 1696 |
| ggt cag gga ata tat gct ttt gtg act ttg gtg gat ggt gtt ccc tac<br>Gly Gln Gly Ile Tyr Ala Phe Val Thr Leu Val Asp Gly Val Pro Tyr<br>                    545                      550                      555 | 1744 |
| agt gat gat cta cgg aaa agc ctc gtt acg acg gtc cgc agt cag att<br>Ser Asp Asp Leu Arg Lys Ser Leu Val Thr Thr Val Arg Ser Gln Ile<br>    560                      565                      570 | 1792 |

-continued

```
ggt gct ttt gct gct cct gaa aag att cat tgg gca cct ggg ctc cct    1840
Gly Ala Phe Ala Ala Pro Glu Lys Ile His Trp Ala Pro Gly Leu Pro
            575                 580                 585 aag aca cga agt ggg aag atc atg cga aga atc tta aga aaa atc gca    1888
Lys Thr Arg Ser Gly Lys Ile Met Arg Arg Ile Leu Arg Lys Ile Ala
        590                 595                 600 tcc agg caa cta gat gag ctc ggc gac acg agc acg ctt gct gac ccc    1936
Ser Arg Gln Leu Asp Glu Leu Gly Asp Thr Ser Thr Leu Ala Asp Pro
605                 610                 615                 620 ggt gtt gtg gac cag ctg att gca ctc agt gac agc taatctatcg         1982
Gly Val Val Asp Gln Leu Ile Ala Leu Ser Asp Ser
                625                 630 gctatgtggg aggggtgag aca                                            2005

<210> SEQ ID NO 4
<211> LENGTH: 632
<212> TYPE: PRT
<213> ORGANISM: Zea mays

<400> SEQUENCE: 4

Met Tyr Gln Lys Ser Ile Asp Asp Pro Ala Gly Phe Trp Ser Glu Ile
  1               5                  10                  15

Ala Asp Glu Phe Tyr Trp Lys Gln Lys Trp Ser Pro Asp Asn Val Cys
             20                  25                  30

Ala Glu Asn Leu Asp Val Thr Lys Gly Pro Ile Met Ile Glu Trp Phe
         35                  40                  45

Lys Gly Gly Lys Thr Asn Ile Cys Tyr Asn Ala Val Asp Arg Asn Val
     50                  55                  60

Glu Ala Gly Asn Gly Asp Lys Ile Ala Met Tyr Trp Glu Gly Asn Glu
 65                  70                  75                  80

Pro Ser Gln Asp Gly Lys Leu Thr Tyr Ser Glu Leu Leu Glu Lys Val
                 85                  90                  95

Cys Gln Leu Ser Asn Tyr Leu Lys Ser Val Gly Val Arg Lys Gly Asp
            100                 105                 110

Ala Val Val Ile Tyr Leu Pro Met Leu Met Glu Leu Pro Ile Ala Met
        115                 120                 125

Leu Ala Cys Ala Arg Ile Gly Val Val His Ser Val Phe Ala Gly
    130                 135                 140

Phe Ser Ala Asp Ala Leu Ala Gln Arg Val Ile Asp Cys Lys Pro Lys
145                 150                 155                 160

Val Val Ile Thr Cys Asn Ala Val Lys Arg Gly Met Lys Ile Ile Pro
                165                 170                 175

Leu Lys Asp Ile Val Asp Ala Ser Leu Asp Gln Ser Ala Lys Asn Gly
            180                 185                 190

Val Asp Val Gly Ile Cys Leu Thr Tyr Glu Asn Gln Ser Ala Leu Asn
        195                 200                 205

Lys Val Asp Thr Arg Arg Lys Thr Gly Arg Asp Val Trp Trp Gln Asp
    210                 215                 220

Val Val Pro Asp Phe Pro Thr Lys Cys Asp Val Glu Trp Val Asp Ala
225                 230                 235                 240

Glu Asp Pro Leu Phe Leu Leu Tyr Thr Ser Gly Ser Thr Gly Lys Pro
                245                 250                 255

Lys Gly Val Leu His Thr Thr Gly Gly Tyr Met Val Tyr Ser Ala Thr
            260                 265                 270

Thr Phe Lys His Ala Phe Asp Tyr Lys Pro Thr Asp Ile Tyr Trp Cys
```

-continued

```
                    275                     280                     285
Thr Ala Asp Cys Gly Trp Ile Thr Gly His Ser Tyr Val Thr Tyr Gly
    290                     295                 300

Pro Leu Leu Asn Gly Ala Thr Val Leu Val Phe Glu Gly Ala Pro Asn
305                 310                 315                     320

Tyr Pro Asp Pro Gly Arg Cys Trp Asp Ile Val Asp Lys Tyr Gly Val
                325                 330                 335

Thr Ile Phe Tyr Thr Ala Pro Thr Leu Ile Arg Ser Leu Met Arg Asp
            340                 345                 350

Gly Thr Glu Tyr Val Ala Arg Tyr Ser Arg Lys Ser Leu Arg Val Leu
        355                 360                 365

Gly Ser Val Gly Glu Pro Ile Asn Pro Thr Ala Trp Arg Trp Phe Tyr
    370                 375                 380

Asp Val Ile Gly Asp Ser Arg Cys Pro Ile Ser Asp Thr Trp Trp Gln
385                 390                 395                     400

Thr Glu Thr Gly Gly Phe Met Ile Thr Pro Leu Pro Gly Ala Trp Pro
                405                 410                 415

Gln Lys Pro Gly Ser Ala Thr Phe Pro Phe Phe Gly Val Gln Pro Val
            420                 425                 430

Ile Val Asp Glu Lys Gly Arg Glu Met Glu Gly Glu Cys Ser Gly Tyr
        435                 440                 445

Leu Cys Ile Lys Lys Ser Trp Pro Gly Ala Phe Arg Thr Leu Tyr Gly
    450                 455                 460

Asp Lys Glu Arg Tyr Glu Thr Thr Tyr Phe Lys Pro Phe Ala Gly Tyr
465                 470                 475                     480

Tyr Phe Ser Gly Asp Gly Cys Ser Arg Asp Lys Asp Gly Tyr His Trp
                485                 490                 495

Leu Thr Gly Arg Val Asp Asp Val Ile Asn Val Ser Gly His Arg Ile
            500                 505                 510

Gly Thr Ala Glu Val Glu Ser Ala Leu Val Ser His Pro Lys Cys Ala
        515                 520                 525

Glu Ala Ala Val Val Gly Ile Asp His Glu Val Lys Gly Gln Gly Ile
    530                 535                 540

Tyr Ala Phe Val Thr Leu Val Asp Gly Val Pro Tyr Ser Asp Asp Leu
545                 550                 555                     560

Arg Lys Ser Leu Val Thr Thr Val Arg Ser Gln Ile Gly Ala Phe Ala
                565                 570                 575

Ala Pro Glu Lys Ile His Trp Ala Pro Gly Leu Pro Lys Thr Arg Ser
            580                 585                 590

Gly Lys Ile Met Arg Arg Ile Leu Arg Lys Ile Ala Ser Arg Gln Leu
        595                 600                 605

Asp Glu Leu Gly Asp Thr Ser Thr Leu Ala Asp Pro Gly Val Val Asp
    610                 615                 620

Gln Leu Ile Ala Leu Ser Asp Ser
625                 630
```